(12) United States Patent
Hayashi et al.

(10) Patent No.: US 9,655,987 B2
(45) Date of Patent: May 23, 2017

(54) STERILIZATION SYSTEM AND GAS FILLING METHOD

(75) Inventors: Hirofumi Hayashi, Wakayama (JP); Ryuichi Iwasaki, Wakayama (JP)

(73) Assignee: NOXILIZER INC., Baltimore, MD (US)

( * ) Notice: Subject to any disclaimer, the term of this patent is extended or adjusted under 35 U.S.C. 154(b) by 588 days.

(21) Appl. No.: 14/127,351

(22) PCT Filed: Jun. 20, 2012

(86) PCT No.: PCT/JP2012/004009
§ 371 (c)(1),
(2), (4) Date: Dec. 18, 2013

(87) PCT Pub. No.: WO2012/176448
PCT Pub. Date: Dec. 27, 2012

(65) Prior Publication Data
US 2014/0119989 A1 May 1, 2014

(30) Foreign Application Priority Data

Jun. 21, 2011 (JP) ................................. 2011-137186

(51) Int. Cl.
*A61L 2/20* (2006.01)
*A61L 2/26* (2006.01)
(Continued)

(52) U.S. Cl.
CPC ...... *A61L 2/26* (2013.01); *A61L 2/14* (2013.01); *A61L 2/20* (2013.01); *C01B 21/36* (2013.01);
(Continued)

(58) Field of Classification Search
CPC ..... A61L 2/14; A61L 2/20; A61L 2/24; A61L 2/26; A61L 2202/14; A61L 2202/24; A61L 2202/25
See application file for complete search history.

(56) References Cited

U.S. PATENT DOCUMENTS

2004/0184950 A1* 9/2004 McVey ............... A61L 2/208
422/4
2007/0014686 A1 1/2007 Arnold et al.
(Continued)

FOREIGN PATENT DOCUMENTS

JP 58-162276 9/1983
JP 1-268557 10/1989
(Continued)

OTHER PUBLICATIONS

International Search Report issued Aug. 14, 2012 in International (PCT) Application No. PCT/JP2012/004009.

*Primary Examiner* — Timothy Cleveland
(74) *Attorney, Agent, or Firm* — Wenderoth, Lind & Ponack, L.L.P.

(57) ABSTRACT

The sterilization system includes a plurality of spaces to be sterilized by a sterilization process; a gas supply source generating nitrogen dioxide gas; a piping system and a valve device; a nitrogen dioxide gas sensor; and a control device. The control device performs a gas filling process in which each of the plurality of spaces to be sterilized is connected to the gas supply source one by one for a first predetermined length of time and successively filled with the nitrogen dioxide gas by controlling the valve device, and when the concentration of the nitrogen dioxide gas in a space to be sterilized that is being filled with gas is detected by the sensor to have reached a predetermined level, the control device performs control such that the subsequent gas filling process is performed with this space to be sterilized being excluded from the gas filling process.

5 Claims, 5 Drawing Sheets

(51) Int. Cl.
  *C01B 21/36*    (2006.01)
  *A61L 2/14*     (2006.01)
(52) U.S. Cl.
  CPC ....... *A61L 2202/24* (2013.01); *A61L 2202/25* (2013.01)

(56) References Cited

U.S. PATENT DOCUMENTS

| | | |
|---|---|---|
| 2008/0152544 A1 | 6/2008 | McVey et al. |
| 2008/0317626 A1 | 12/2008 | Arnold et al. |
| 2011/0008207 A1* | 1/2011 | Arai .......................... A61L 2/20 422/28 |
| 2011/0318225 A1 | 12/2011 | Arnold et al. |

FOREIGN PATENT DOCUMENTS

| | | |
|---|---|---|
| JP | 2002-102318 | 4/2002 |
| JP | 2006-523821 | 10/2006 |
| JP | 2009-542333 | 12/2009 |
| JP | 2010-202448 | 9/2010 |
| JP | 2011-4802 | 1/2011 |
| WO | 2009/119593 | 10/2009 |

* cited by examiner

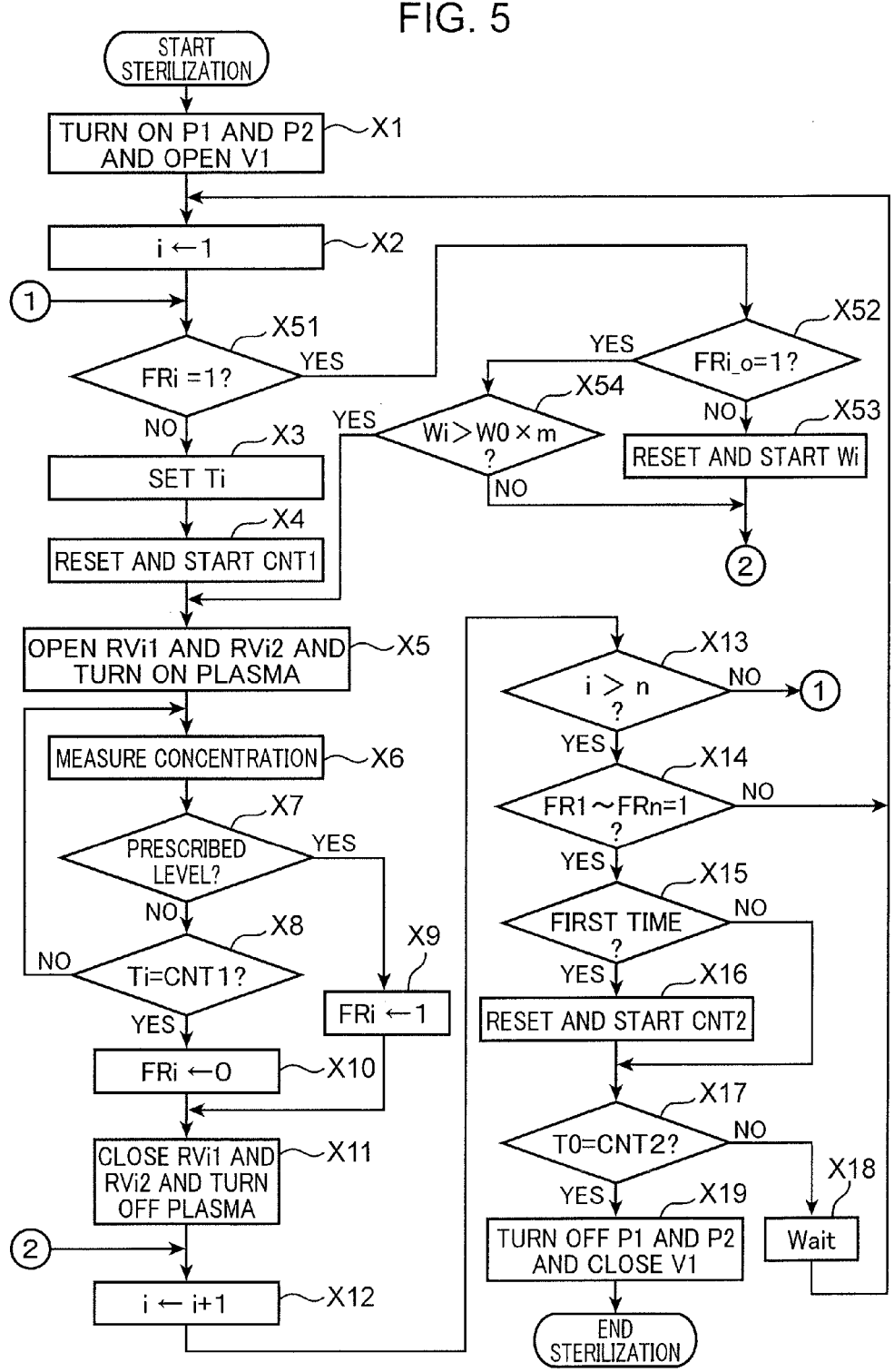

STERILIZATION SYSTEM AND GAS FILLING METHOD

TECHNICAL FIELD

The present invention relates to a system for sterilizing a space that is the object of sterilization such as a clean room or an isolator by filling the space with nitrogen dioxide gas as means of sterilization, and a gas filling method.

BACKGROUND ART

A sterilization apparatus sterilizes objects to be processed accommodated in a processing chamber such as medical tools or food package materials to a high degree. Patent Document 1, for example, shows the use of nitrogen oxide (NOx) gas for the processing of the objects. The sterilization apparatus of Patent Document 1 is an apparatus that uses nitrogen oxide gas for sterilizing coliform *bacillus* present on food. The nitrogen oxide gas is produced by introducing a gas mixture of nitrogen and oxygen into a plasma generating chamber and turning the gas mixture into plasma.

The sterilization efficiency is not necessarily high with the use of nitrogen oxide gas and there were needs for improvements in the sterilization efficiency. Through vigorous research, the applicants of the present application have found out that it is nitrogen dioxide ($NO_2$), one of various nitrogen oxides (NOx), that substantially contributes to sterilization of bacteria. The applicants have proposed a method of producing high purity nitrogen dioxide gas, and an apparatus for storing the nitrogen dioxide gas thus produced by this method in Patent Document 2.

The sterilization apparatus of Patent Document 2 achieves high sterilization effect by the use of nitrogen dioxide gas. This sterilization apparatus, however, is directed to sterilization of medical tools or food package materials as the objects of sterilization. Therefore, after the objects are accommodated in the processing chamber and a substantial vacuum is drawn in the chamber, the chamber is filled with nitrogen dioxide gas to a concentration as high as several tens of thousands ppm. The sterilization apparatus can thus sterilize even small parts such as inside of tubes in a short time.

Meanwhile, there are needs for other sterilization applications that do not require such a high degree of sterilization, but require uniform sterilization of a wide space with people in it such as a clean room as the object of sterilization, with a safe, low concentration of nitrogen dioxide gas, even though it may take a long time. There are other operations other than sterilization such as disinfection or decontamination for reducing microorganisms, but these will herein all be inclusively called "sterilization".

Patent Document 1: Japanese Patent Application Laid-open No. S58-162276
Patent Document 2: Japanese Patent Application Laid-open No. 2010-202448

SUMMARY OF THE INVENTION

An object of the present invention is to provide a sterilization system with which a plurality of relatively wide spaces to be sterilized can be evenly sterilized with a relatively low concentration of nitrogen dioxide gas.

A sterilization system according to one aspect of the present invention includes:
a plurality of spaces to be sterilized by a sterilization process;
a gas supply source generating nitrogen dioxide gas to be used for the sterilization process;
a piping system and a valve device interposed between the gas supply source and the spaces to be sterilized;
a sensor detecting a concentration of the nitrogen dioxide gas in the spaces to be sterilized; and
a control device configured to control the valve device to repeatedly perform a cycle of gas filling process in which each of the plurality of spaces to be sterilized is connected to the gas supply source one by one for a first predetermined length of time and successively filled with the nitrogen dioxide gas, and configured, when the concentration of the nitrogen dioxide gas in a space to be sterilized that is being filled with gas is detected by the sensor to have reached a predetermined level, to perform control such that a next cycle of the gas filling process is performed with this space to be sterilized being excluded from the gas filling process.

A gas filling method in a sterilization system according to another aspect of the present invention is a method of filling a plurality of spaces to be sterilized by a sterilization process with nitrogen dioxide gas to be used for the sterilization process, including the steps of:
performing a cycle of gas filling process of successively filling each of the plurality of spaces to be sterilized with the nitrogen dioxide gas one by one for a first predetermined length of time;
detecting a concentration of the nitrogen dioxide gas in the plurality of spaces to be sterilized and specifying a gas-filled space to be sterilized in which the nitrogen dioxide gas concentration has reached a predetermined level; and
performing further a cycle of gas filling process of successively filling each of the plurality of spaces to be sterilized except for the specified gas-filled space to be sterilized, with the nitrogen dioxide gas one by one for the first predetermined length of time.

The objects, features, and advantages of the present invention will become more apparent by the following detailed description and accompanying drawings.

BRIEF DESCRIPTION OF THE DRAWINGS

FIG. 5 is a flowchart showing one example of the sterilization operation in FIG. 4.

BEST MODE FOR CARRYING OUT THE INVENTION

Figure 1:
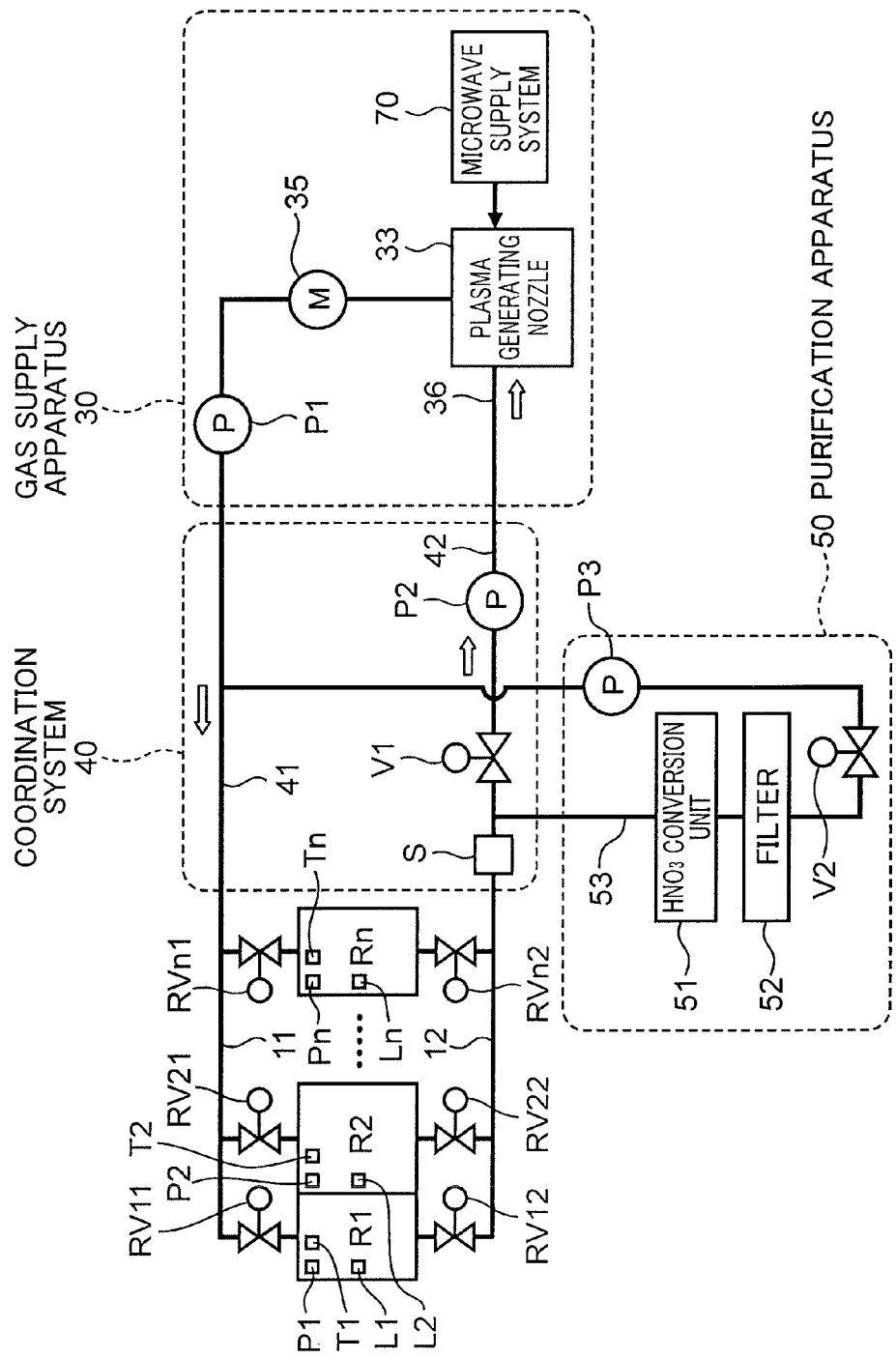
FIG. 1 is a block diagram of a sterilization system according to one embodiment of the present invention.

FIG. 1 is a block diagram of a sterilization system 1 according to one embodiment of the present invention. This sterilization system 1 includes a plurality of clean rooms R1, R2, . . . Rn (hereinafter denoted at reference symbol R when referred to collectively) used for production of pharmaceutical products as processing chambers to be sterilized (space to be sterilized), and sterilizes the clean rooms R by applying nitrogen dioxide ($NO_2$) gas generated by plasma in the rooms during a time zone such as a weekend when the clean rooms R are not in use. Roughly speaking, this sterilization system 1 is configured to include the clean rooms R, a gas supply apparatus 30, a coordination system 40, and a purification apparatus 50.

In this embodiment, an example is shown in which nitrogen dioxide gas is used as sterilizer, which is generated from air as a material gas through the plasma process. Therefore, the sterilization system 1 of this embodiment enables a cost reduction, as handling of the material gas is easy, and can produce nitrogen dioxide that is harmful to human body in a necessary amount at a place where it is required. The processing chamber may be an isolator or the like that has glass walls with rubber gloves attached thereto to allow manual handling of testing tools arranged in the chamber through the rubber gloves.

The clean rooms R have inner space that is appropriately sealed up during sterilization to achieve high airtightness. An operator can work inside this inner space. Each of the clean rooms R1 to Rn is equipped with a suitable lock device L1 to Ln to prevent unwanted human access during sterilization and an alarm device (not shown) that displays a warning message saying that the sterilization is in process. Each clean room R may have any volume or size.

The gas supply apparatus 30 produces $NO_2$ gas or increases the concentration of $NO_2$ gas by ionizing a material gas that is present in the closed space formed by the clean rooms R, the gas supply apparatus 30, and the coordination system 40 into a plasma. The material gas inside the closed space is mainly the air introduced by opening and closing the clean rooms R or low-concentration $NO_2$ gas that has returned from the clean rooms R to the gas supply apparatus 30.

The gas supply apparatus 30 includes a plasma generating nozzle 33, a microwave supply system 70, a gas flowmeter 35, a pump P1, and a piping system 36. The plasma generating nozzle 33, the gas flowmeter 35, and the pump P1 are provided in this order in the piping system 36. As air or low-concentration $NO_2$ gas introduced from the clean rooms R through the coordination system 40 passes through respective units in the order mentioned above, it turns into $NO_2$ gas and fills the clean rooms R through the coordination system 40.

The plasma generating nozzle 33 provides a concentrated electric field for generating plasma (ionized gas). The material gas (containing nitrogen and oxygen) flowing through the piping system 36 is ionized and turned into $NO_2$ gas as it passes through the concentrated electric field of the plasma generating nozzle 33. To generate the plasma, microwave energy is used in this embodiment. The microwave supply system 70 provides the microwave energy to the plasma generating nozzle 33.

Figure 2:
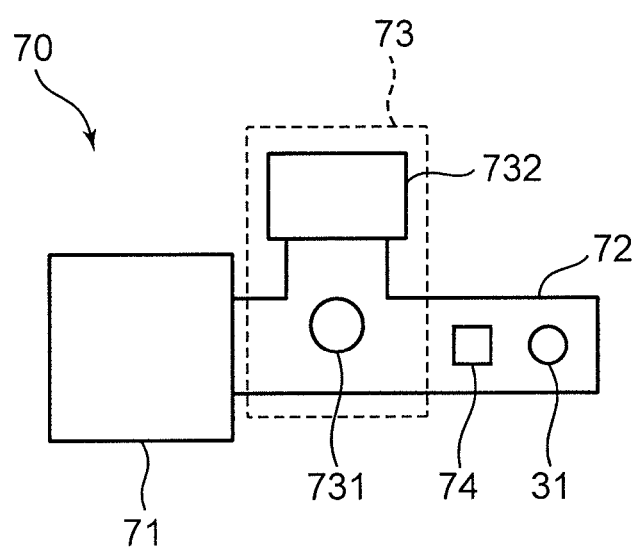
FIG. 2 is a schematic block diagram of the configuration of a microwave supply system in the sterilization system shown in FIG. 1.

FIG. 2 is a schematic block diagram of the configuration of the microwave supply system 70. The microwave supply system 70 is an apparatus for producing microwave energy and supplying the energy to the plasma generating nozzle 33, and includes a microwave generator 71 for generating microwave energy and a waveguide 72 for the microwave to propagate through. The plasma generating nozzle 33 is mounted in this waveguide 72. An isolator 73 and a coupler 74 are provided between the microwave generator 71 and the waveguide 72.

The microwave generator 71 includes a microwave generation source such as magnetron that generates microwaves of, for example, 2.45 GHz, and an amplifier that adjusts the intensity of microwaves generated from the microwave generation source to a predetermined output intensity. In this embodiment, a continuous variable microwave generator 71 capable of outputting microwave energy of, for example, 1 W to 3 kW, can preferably be used.

The waveguide 72 is made of non-magnetic metal such as aluminum and has an elongated tubular shape with a rectangular cross section. Microwaves generated by the microwave generator 71 are propagated through the waveguide along the longitudinal direction. The isolator 73 is a device that isolates the input and the output from each other to prevent microwaves reflected from the waveguide 72 from entering the microwave generator 71, and includes a circulator 731 and a dummy load 732. The circulator 731 directs the microwaves generated by the microwave generator 71 toward the waveguide 72, while directing reflected microwaves toward the dummy load 732, with magnetic force. The dummy load 732 absorbs reflected microwaves and converts the microwave energy into heat. The coupler 74 measures the intensity of the microwave energy.

The microwave supply system 70 of this embodiment is adjusted such that the microwave receptivity is the highest at the plasma generating nozzle 33, while the microwaves are reflected as little as possible to the microwave generator 71, by suitably tuning the distance from the microwave generator 71 to the plasma generating nozzle 33 relative to the frequency of the microwaves. However, at least one of a tuner disposed upstream of the plasma generating nozzle 33 in the microwave propagation direction, or a sliding short disposed downstream in the microwave propagation direction may be mounted to the waveguide 72 for additional tuning to deal with variations in the components, or for even more precise tuning.

The tuner is a device that includes a stub protrudable into the waveguide 72 for making adjustments such that microwaves are reflected as little as possible, i.e., such that the microwave energy is consumed maximally at the plasma generating nozzle 33. The coupler 74 can be utilized for the adjustments. The sliding short is a component that closes the distal end of the waveguide 72 (downstream end in the microwave propagation direction) and moves along the axial direction, or the microwave propagation direction, of the waveguide 72 to adjust the standing wave pattern by changing the reflecting positions of the microwaves.

Referring back to FIG. 1, the coordination system 40 is a system for communicating the clean rooms R and the gas supply apparatus 30 and for connecting a purification apparatus 50 that detoxifies the $NO_2$ gas that has been used for sterilization and not required any more to the clean rooms R. The coordination system 40 includes solenoid valves RV11 to RVn1, RV12 to RVn2, a solenoid valve V1, a pump P2, a concentration sensor S, and piping systems 11, 12, 41, and 42.

One end (upstream end) of the piping system 41 is connected to the pump P1 of the gas supply apparatus 30, while the other end (downstream end) is connected to the common piping system 11 on the side of the clean rooms R. One end (upstream end) of the piping system 42 is connected to the common piping system 12 on the side of the clean rooms R, while the other end (downstream end) is connected to the plasma generating nozzle 33 (piping system 36) of the gas supply apparatus 30. The pump P2 is disposed downstream of this piping system 42. The pump P2 is operated together with the pump P1 for circulating the $NO_2$ gas from the gas supply apparatus 30 to and from the clean rooms R during the sterilization.

The concentration sensor S that measures the concentration of $NO_2$ gas inside the clean rooms R is provided in the piping system 42. The solenoid valve V1 is mounted to the piping system 42, and opened during the sterilization process, while it is closed during the detoxification process of $NO_2$ gas by the purification apparatus 50 as will be described later. Both of the two pumps P1 and P2 are turned on during the sterilization process.

The purification apparatus 50 is an apparatus for detoxifying $NO_2$ gas that has been used for the sterilization, as mentioned above. Detoxified gas is circulated from the purification apparatus 50 back to the clean rooms R. The purification apparatus 50 includes an $HNO_3$ conversion unit 51, a filter 52, a solenoid valve V2, a pump P3, and a piping system 53.

One end (upstream end) of the piping system 53 is connected to the downstream side of the concentration sensor S in the coordination system 40, while the other end (downstream end) is connected to the piping system 41 on the return side in the coordination system 40. The $NO_2$ gas collected via the concentration sensor S to be detoxified is sucked by the pump P3 through the $HNO_3$ conversion unit 51 and the filter 52, and returned from the pump P3 to the clean rooms R after being detoxified.

The $HNO_3$ conversion unit 51 converts $NO_2$ contained in the gas after the sterilization process into $HNO_3$. For the conversion, the $HNO_3$ conversion unit 51 includes an ozone generator that generates ozone ($O_3$), and a water introducer for supplying water ($H_2O$). Adding $O_3$ and $H_2O$ to the $NO_2$ gas passing through the $HNO_3$ conversion unit 51 chemically converts the gas containing $HNO_3$.

The filter 52 adsorbs $HNO_3$ in the gas. The filter 52 may be made, for example, from a ceramic base material having a honeycomb structure with a coating layer that adsorbs nitric acid. The pump P3 sucks $NO_2$ gas out of the clean rooms R with a negative pressure that allows the $HNO_3$ conversion unit 51 and the filter 52 to function appropriately. The pump P3 is provided in order to increase the flow rate during the detoxification process as compared to the flow rates of the pumps P1 and P2 used during the generation of $NO_2$ gas. $HNO_3$ may be removed by other techniques other than filter adsorption. Detoxification of $NO_2$ gas may be achieved by using other techniques such as dissolution in solvent.

As mentioned above, the plurality of clean rooms R are formed to have a desired size, so that the volume to be filled with $NO_2$ gas varies depending on the space taken up by the equipment stored in the rooms, etc. Each clean room R has gas introduction holes and gas discharge holes in an upper part and a lower part, respectively, for introduction of $NO_2$ gas that is heavier than air and for return of detoxified gas.

The gas introduction holes of the clean rooms R1, R2, . . . Rn are connected to the piping system 11 via the solenoid valves RV11, RV21, . . . RVn1 (valve device). The piping system 11 is connected to the piping system 41 of the coordination system 40. The gas discharge holes of the clean rooms R1 to Rn are connected to the piping system 12 via the solenoid valves RV12, RV22, . . . RVn2 (valve device). The piping system 12 is connected to the piping system 42 of the coordination system 40.

With the pairs of solenoid valves RV11 to RVn1 and RV12 to RVn2 being opened, $NO_2$ gas sent out by the pump P1 of the gas supply apparatus 30, or the detoxified gas sent out by the pump P3 of the purification apparatus 50, is supplied to the clean rooms R1 to Rn, and air or used $NO_2$ gas in the clean rooms R1 to Rn are sucked out by the pump P2 or pump P3.

Figure 3:
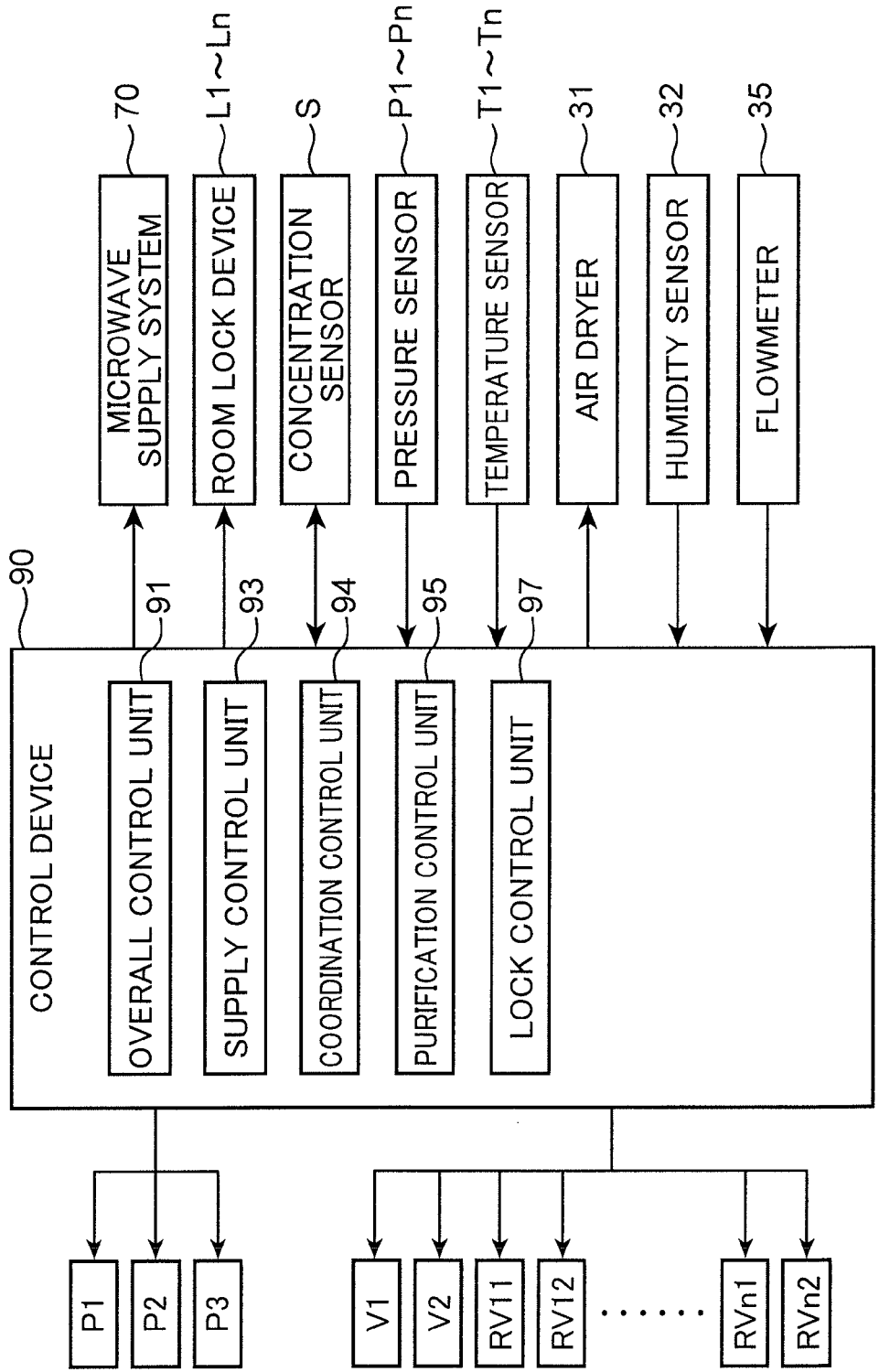
FIG. 3 is a block diagram showing an electric control configuration of the sterilization system.

Next, the electrical control configuration of the sterilization system 1 will be described with reference to FIG. 3. Although not shown in FIG. 1, the sterilization system 1 includes a control device 90 for electrically controlling the operation of the sterilization system 1. The control device 90 includes a CPU (central processing unit) that processes information, and operates such as to have the functional units shown in FIG. 3, by a software application programmed to perform the operation control of the sterilization system 1 being executed. The control device 90 functionally includes an overall control unit 91, a supply control unit 93, a coordination control unit 94, a purification control unit 95, and a lock control unit 97.

The overall control unit 91 manages the overall operation modes of the sterilization system 1 and gives control signals to each of the control units 93, 94, 95, and 97 to instruct to change or maintain the operation mode. The concentration data of $NO_2$ gas inside the clean rooms R measured by the concentration sensor S, pressure data measured by pressure sensors SP1 to SPn of the clean rooms R, and temperature data measured by temperature sensors T1 to Tn of the clean rooms R are input to the overall control unit 91. The overall control unit 91 manages the operation modes of the sterilization system 1, sets a mode and transfers necessary data to the respective control units 93, 94, 95, and 97 based on these concentration data, pressure data, temperature data, and time data given from a timer device (not shown) or the like.

The supply control unit 93 controls the gas supply apparatus 30 to increase the concentration of $NO_2$ gas as the gas is circulated between the gas supply apparatus 30 and the clean rooms R. For this control, the supply control unit 93 gives control signals to the microwave supply system 70 and the pump P1 to start and stop. The supply control unit 93 controls the rpm of the pump P1 when the pump is running in accordance with the measurement results of the flowmeter 35. The supply control unit 93 thus generates $NO_2$ gas from the plasma stably generated by the plasma generating nozzle 33 during the period in which $NO_2$ gas is produced. The supply control unit 93 drives an air dryer 31 in response to the detection results from a humidity sensor 32 of the gas introduced from the clean rooms R, and monitors the air dryer 31 for abnormality.

The coordination control unit 94 controls the solenoid valves RV11 to RVn1 and RV12 to RVn2 of the coordination system 40 in pairs. The coordination control unit 94 also controls the pump P2 and the solenoid valve V1 to switch one clean room R successively from another so that $NO_2$ gas from the gas supply apparatus 30 is supplied to the clean rooms one by one. The coordination control unit 94 closes the solenoid valve V1 disposed in the piping system 42 for the return from the clean rooms R to allow for removal of $NO_2$ gas from the respective clean rooms R by the purification apparatus 50.

The common concentration sensor S measures the concentration of the $NO_2$ gas inside one of the clean rooms R that is selected by selectively opening one of the pairs of solenoid valves RV11 to RVn1 and RV12 to RVn2 when $NO_2$ gas is flowing into or out of the respective clean room R. The measurement values are given to the coordination control unit 94, purification control unit 95, and lock control unit 97. The common concentration sensor S is thus used for the respective clean rooms R so as to minimize the effects of sensor variations.

The purification control unit 95 controls the solenoid valve V2 of the purification apparatus 50, and controls the pump P3 to remove $NO_2$ gas from the clean rooms R, detoxifies the gas, and returns the gas to the clean rooms R. During the detoxification process, the purification control unit 95 drives the pump P3 and opens the solenoid valve V2 to remove $NO_2$ gas from the clean rooms R, and detoxifies the gas by converting $NO_2$ to $N_2$. The purification control unit 95 may drive the pump P1 of the gas supply apparatus 30 and opens the solenoid valve V1 at a stage when the $NO_2$ gas being discharged from the clean room R has been purified to some extent, to release any remaining $NO_2$ gas in the gas supply apparatus 30 into the clean room R, after which the $NO_2$ gas may be taken into the purification apparatus 50 to be detoxified.

The lock control unit 97 controls the operation of lock devices L1 to Ln of the respective clean rooms R1 to Rn. The lock devices L1 to Ln are devices that lock the doors of entrances/exits (not shown) of the clean rooms R1 to Rn. These doors are locked by these lock devices L1 to Ln during the series of sterilization process for preventing unwanted access of human beings for securing safety.

Figure 4:
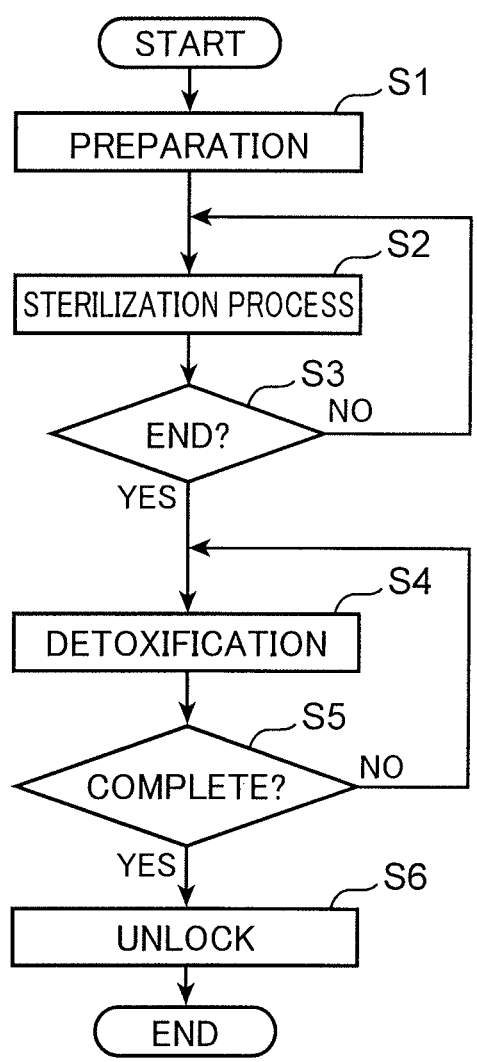
FIG. 4 is a flowchart for explaining the overall control operation of the sterilization system.

FIG. 4 is a flowchart for explaining the overall control operation performed by the overall control unit 91 with the use of the functions of the respective control units 93, 94, 95, and 97. At step S1, preparation is made, wherein air conditioner ducts that lead to the clean rooms R1 to Rn are closed, operators leave the clean rooms R, and the lock devices L1 to Ln are turned on. The overall control unit 91 releases an interlock after confirming that the lock control unit 97 has turned on the lock devices L1 to Ln, to allow for execution of the sterilization operation.

At step S2, the overall control unit 91 instructs the purification control unit 95 to close the solenoid valve V2, instructs the coordination control unit 94 to open the solenoid valve V1, and drives the pump P2, to form a gas circulation route between the gas supply apparatus 30 and the clean rooms R. The overall control unit 91 also instructs the supply control unit 93 to drive the microwave supply system 70, and drives the pump P1. The clean rooms R are thus sterilized, and the sterilization process is continued until it is determined at step S3 that a predetermined length of time of, e.g. 10 hours, has passed.

When the sterilization is complete (YES at step S3), the overall control unit 91 instructs the coordination control unit 94 to close the solenoid valve V1 at step S4 to form a gas circulation route between the purification apparatus 50 and the clean rooms R. The overall control unit 91 also instructs the purification control unit 95 to open the solenoid valve V2 and drives the pump P1, to perform detoxification of $NO_2$ gas that has been used for the sterilization. In the sterilization process of step S2, as will be described later, the concentration of $NO_2$ gas in the circulation route initially increases, and when the concentration reaches a certain level, it is kept at that level. Therefore, when the sterilization process is ended at step S3, the overall control unit 91 has already instructed the supply control unit 93 to stop or reduce the power of the microwave supply system 70. The pump P1 is operated throughout the sterilization process for cooling the electrodes in the plasma generating nozzle 33.

At step S5, the overall control unit 91 determines whether or not the concentration of the $NO_2$ gas in all of the clean rooms R has reduced to a decision making threshold value of 1 ppm or lower from the measurement results of the concentration sensor S. If the $NO_2$ gas concentration is not 1 ppm or lower (NO at step S5), the overall control unit 91 returns to step S4 and instructs the purification control unit 95 to continue the detoxification process. If the $NO_2$ gas concentration is 1 ppm or lower (YES at step S5), the overall control unit 91 determines that the clean rooms R are now accessible, and determines that the detoxification process has completed. At step S6, the overall control unit 91 instructs the lock control unit 97 to turn off the lock devices L1 to Ln, or turns off the alarm lamp to indicate that the clean rooms R are now accessible, and ends the process.

FIG. 5 is a flowchart for explaining the sterilization operation at step S2 in detail. Generally, the sterilization process may be performed such that the clean rooms R are filled with $NO_2$ gas one by one to a prescribed concentration of, for example, 200 ppm to achieve sterilization. Instead, in this embodiment, a cycle of filling process of filling one clean room R after another with a small amount of $NO_2$ gas is repeated until the gas concentration of the clean rooms R reaches the prescribed level. Moreover, the filling time is set individually for each clean room R in accordance with the sizes of the clean rooms R and the amount of the contents, i.e., the actual volume to be filled with $NO_2$ gas, so that the gas concentration will increase substantially uniformly in all of the clean rooms R. Thus, a basic filling time Ti (first length of time) is preset in accordance with the volume for each of the clean rooms Ri (i=1 to n).

In the example of FIG. 1, for example, relatively small clean rooms R1 and Rn have a filling time Ti of 1 minute, while a relatively large clean room R2 has two minutes. The filling time Ti is not a period of time with which each clean room Ri can be filled with a sufficient concentration of gas by one filling operation. One cycle of filling process, in which the filling operation is performed for a duration of the filling time Ti for one clean room Ri after another, is repeated several times. When the $NO_2$ gas concentration has reached the predetermined level in any of the clean rooms Ri (gas-filled space to be sterilized), this clean room is excluded from the object to be filled with gas, and one cycle of filling process is carried out again. One example of specific control flow in accordance with such a control method will be described below.

At step X1, the overall control unit 91 instructs the supply control unit 93 to drive the pump P1, and instructs the coordination control unit 94 to drive the pump P2, and opens the solenoid valve V1, to connect the coordination system 40 with the gas supply apparatus 30. At step X2, the overall control unit 91 sets an initial value i of 1, the "i" being a variable representing the room number of the clean rooms R. At step X51, the overall control unit 91 checks the flag FRi that indicates whether or not the gas concentration has reached a prescribed level in the i-th clean room Ri. If the flag FRi has been reset to 0, i.e., if the gas concentration has not reached a prescribed level in the clean room Ri (NO at step X51), the process goes to step X3. The flag FRi is initially reset to 0. At step X3, the overall control unit 91 sets a filling time Ti corresponding to the room number i.

When it is ready for the sterilization process, the overall control unit 91 resets and starts a timer CNT1 at step X4. At step X5, the overall control unit 91 instructs the supply control unit 93 to operate the microwave supply system 70 to generate $NO_2$ gas from the plasma generating nozzle 33. The overall control unit 91 instructs the coordination control unit 94 to open the solenoid valves RVi1 and RVi2 of the clean room Ri with the room number i, to start filling the room with the generated $NO_2$ gas.

At step X6, the overall control unit 91 obtains concentration data of $NO_2$ gas in the clean room Ri measured by the concentration sensor S. At step X7, the overall control unit 91 determines whether or not the measured gas concentration is the prescribed level or higher. If the gas concentration has not reached the prescribed level yet, the overall control unit 91 determines whether or not the measurement time of the timer CNT1 has reached the filling time Ti (step X8), and if not (NO at step X8), the process goes back to step X6, to continue filling the clean room Ri with the $NO_2$ gas.

On the other hand, if the $NO_2$ gas concentration is the prescribed level or higher at step X7 (YES at step X7), the overall control unit 91 sets the flag FRi to 1 at step X9. If the prescribed filling time Ti has been reached at step X8 (YES at step X8), i.e., if the prescribed concentration level has not been reached within the filling time Ti of this cycle, the overall control unit 91 resets the flag FRi to 0 at step X10. The process goes from step X9 and step X10 to step X11, where the overall control unit 91 instructs the coordination control unit 94 to close the solenoid valves RVi1 and RVi2 of the clean room Ri with the room number i, and instructs the supply control unit 93 to stop the microwave supply system 70, to end the filling of $NO_2$ gas.

It takes about 10 seconds from the time when microwave supply system 70 is turned on until the plasma generating nozzle 33 operates stably, so that there is some delay in the filling process. There is no significant problem even if the plasma nozzle is turned on at step X5 and turned off at step X11. However, the supply control unit 93 should preferably stop generation of actual microwaves after a predetermined delay time has passed after it was instructed by the overall control unit 91 to stop the microwave supply system 70. That is, the microwave supply system 70 would operate continuously if the microwave supply system 70 was operating during the filling process for the previous clean room Ri and if it is turned on at step X5 in the filling process for the next clean room Ri+1. The pump P1 is operated during the sterilization process to create a flow of gas in the piping system 36 so that the plasma generating nozzle 33 is cooled, as mentioned above. Therefore, instead of completely stopping generation of microwaves, power may be reduced, so that the nozzle can quickly start to operate again.

In determining the gas concentration at step X7, there may be set two thresholds, instead of one. If the flag FRi is set to 1, for example, i.e., if the concentration has already reached the prescribed level, the threshold, based on which it is determined whether or not the concentration is decreasing, is set low. If the flag FRi is set to 0, i.e., if the concentration has not reached the prescribed level yet, the threshold, based on which it is determined whether or not the concentration is increasing, is set high. Setting of such thresholds can give hysteresis to the determination of gas concentration, so that frequent turning on and off of the plasma nozzle around the threshold is prevented, and the control is made stable.

Next, the overall control unit 91 adds 1 to the variable i, to renew the room number to a next one (step X12). At the next step X13, the overall control unit 91 determines whether or not the variable i has exceeded the maximum room number n. If the room number n has not been exceeded (NO at step X13), the process goes back to step X3, to fill the next clean room Ri+1 with $NO_2$ gas.

If it is determined at step X13 that all of the clean rooms R1 to Rn have been filled with $NO_2$ gas, the overall control unit 91 determines from flags FR1 to FRn whether or not the gas concentration is the prescribed level or higher in all of the clean rooms R1 to Rn at step X14. If there is left a room in which the concentration has not reached the prescribed level yet (NO at step X14), the process goes back to step X2 to perform one more cycle of gas filling. This one cycle of gas filling process is targeted only to the clean room Ri, for which the flag FRi has been reset to 0. The clean room Ri (gas-filled space to be sterilized), for which the flag FRi has been reset to 1, is excluded from the object to be filled with gas (see also the processes at steps X51 to X54 to be described later).

If the gas concentration is the prescribed level or higher in all of the clean rooms R1 to Rn at step X14 (YES at step X14), the overall control unit 91 determines whether or not it is the first time that this state is achieved (step X15). If it is the first time (YES at step X15), the overall control unit 91 resets and starts a timer CNT2 that measures the duration of the sterilization process, and the process goes to step X17. If it is not the first time (NO at step X15), the overall control unit 91 proceeds directly to step X17.

At step X17, the overall control unit 91 determines whether or not the measurement time of the timer CNT2 has reached a prescribed sterilization process time T0 of, for example, 10 hours, as mentioned above. If the sterilization process time T0 has not been reached yet (NO at step X17), a predetermined time of, for example, 5 minutes (step X18) is waited, and the process goes back to step X2. If the prescribed sterilization process time T0 has passed at step X17 (YES at step X17), the overall control unit 91 instructs the coordination control unit 94 to stop the pump P2, and closes the solenoid valve V1 to separate the coordination system 40 from the gas supply apparatus 30, and instructs the supply control unit 93 to stop the pump P1, to end the process, at step X19.

If the flag FRi is set to 1 at step X51 (YES at step X51), the overall control unit 91 proceeds to step X52 and checks the condition flag FRi_o that indicates the condition of the flag FRi when it was set previously. If this condition flag FRi_o is 0, i.e., if the flag FRi has been set to 1 first time in the determination at step X51 this time ($NO_2$ gas concentration has reached the prescribed level) (NO at step X52), then the overall control unit 91 resets and starts a timer Wi at step X53 and proceeds to step X12 to renew the room number i.

On the other hand, if the condition flag FRi_o is set to 1 at step X52, i.e., if the flag FRi has already been set to 1 at step X51 at previous times, it means that the $NO_2$ gas concentration has already reached the prescribed level (YES at step X52), and the overall control unit 91 determines at step X54 whether or not the count value of the timer Wi indicates that a predetermined monitoring interval W0 (second length of time) of, e.g., 10 minutes, have passed, or that it has reached a multiple m of 10 minutes, for the first time.

If it is the second time or more after a multiple m of 10 minutes, or if it has not reached a multiple m of 10 minutes yet (NO at step X54), the overall control unit 91 proceeds to step X12. Thus filling of $NO_2$ gas, measurement of concentration, and all the other work for the i-th clean room Ri are skipped as the process goes from steps X51 and X52 to step X12 via X53 or X54, so that the next, (i+1)th clean room Ri+1 is specified.

If, at step X54, it is the first time that a multiple m of the monitoring interval W0 has passed (YES at step X54), then the process goes to step X5 and the overall control unit 91 opens the solenoid valves RVi1 and RVi2 of the i-th clean room Ri, and measures the concentration again at step X6. Namely, the concentration is measured every time it is determined for the first time that 10 min, 20 min, 30 min, 40 min, . . . have passed. The plasma nozzle need not be turned on when the process goes from step X54 to step X5, or may be turned on so that a slight amount of $NO_2$ gas is provided, which does not cause any problem.

As described above, the sterilization system 1 of this embodiment is designed for a plurality of relatively wide clean rooms R as the spaces to be sterilized. The overall control unit 91 controls the coordination system 40 to execute the filling process wherein the plurality of clean rooms R are connected to the gas supply apparatus 30 one by one successively for the prescribed filling time Ti (first length of time) to fill each clean room Ri with $NO_2$ gas in a small amount at a time. When one cycle of filling all the clean rooms Ri with gas is complete, the overall control unit 91 executes the next cycle of filling process similarly to that described above. During the gas filling process, the overall control unit 91 monitors the concentration of $NO_2$ gas detected by the concentration sensor S, and when a prescribed concentration is reached in a clean room Ri, filling of gas to that room is ended, and this clean room Ri is excluded from the object to be filled with gas from the next cycle onwards (steps X51-X52-X53, and X54-X12). Thus the clean rooms Ri can be evenly and efficiently sterilized.

As the filling time Ti is preliminarily set (step X3) in accordance with the volume of each clean room Ri in the sterilization system 1 of this embodiment, even if there is a difference in the volume, the gas concentration can be evenly increased as cycles of filling process are repeated.

Also, since the concentration of $NO_2$ gas in every clean room Ri is measured by the same concentration sensor S through a common piping system 12, all the clean rooms Ri, even though they have different sizes (volumes), can be filled with a uniform concentration of gas highly precisely.

In the sterilization system 1, the concentration sensor S is arranged in the common piping system 12. Therefore, when one clean room is excluded from the object to be filled with gas, the concentration of $NO_2$ gas is not detected during the time when that room is excluded from the filling process. However, in this embodiment, the overall control unit 91 connects such a clean room to the coordination system 40 every time a predetermined monitoring interval W0 having a predetermined second length of time passes, and detects concentration by the concentration sensor S (step X54) every multiple m of the interval. Therefore, even if the $NO_2$ gas concentration of the clean room R in question has reduced from the prescribed level as the gas is absorbed by the walls or contents of the clean room R, such a drop in concentration is reliably detected, so that the gas concentration is kept evenly and sterilization is achieved reliably. According to the results of the test conducted by the inventors of the present invention, when the clean room is 100 m$^3$ wide with aluminum frames and PVC walls, the gas concentration lowers by 2% per hour. It is expected to lower more in actual clean rooms.

In the sterilization system 1 of this embodiment, further, the gas supply apparatus 30, coordination system 40, and clean rooms R form a closed space. The gas supply apparatus 30 creates $NO_2$ gas from air in the closed space as a material gas by generating plasma. Therefore, the system does not require complex structures for adjustment of pressure or introduction of outside air to increase the concentration of $NO_2$ gas.

While one embodiment of the present invention has been described above, the invention is not limited to this and may be modified as in the modified embodiments (1) and (2) below.

(1) In the example shown in the embodiment above, air is turned into plasma to generate gas to be used for sterilization, with the use of the microwave supply system 70 and the plasma generating nozzle 33. Another method of generating plasma may be adopted, such as an arc discharge between two electrodes.

(2) While the sterilization process is performed in the clean rooms R at normal pressure in the embodiment described above, the process may be carried out at reduced pressure.

The specific embodiments described above generally contain an invention having the following configurations.

A sterilization system according to one aspect of the present invention, includes a plurality of spaces to be sterilized by a sterilization process;

a gas supply source generating nitrogen dioxide gas to be used for the sterilization process;

a piping system and a valve device interposed between the gas supply source and the spaces to be sterilized;

a sensor detecting a concentration of the nitrogen dioxide gas in the spaces to be sterilized; and a control device configured to control the valve device to repeatedly perform a cycle of gas filling process in which each of the plurality of spaces to be sterilized is connected to the gas supply source one by one for a first predetermined length of time and successively filled with the nitrogen dioxide gas, and configured, when the concentration of the nitrogen dioxide gas in a space to be sterilized that is being filled with gas is detected by the sensor to have reached a predetermined level, to perform control such that a next cycle of the gas filling process is performed with this space to be sterilized being excluded from the gas filling process.

With the configuration described above, in a sterilization system that performs a sterilization process by filling a space that is an object of the sterilization process with nitrogen dioxide ($NO_2$) gas that is generated from the gas supply source, when there is a plurality of spaces to be sterilized, the control device controls the filling of nitrogen dioxide gas in the respective spaces to be sterilized in the following manner. The control device controls the valve device that is interposed along with the piping system between the gas supply source and the spaces to be sterilized such that the plurality of spaces to be sterilized are connected to the gas supply source cyclically one by one for a first predetermined length of time and each of the spaces is filled nitrogen dioxide gas in a small amount at a time. During the filling, the control device monitors the concentration of the nitrogen dioxide gas detected by the sensor, and when the concentration in a space to be sterilized that is being filled with gas reaches a predetermined level of, for example, 200 ppm, the filling of that space is ended and this space is excluded from the gas filling process from a next cycle onwards. Thus a plurality of relatively wide spaces to be sterilized can be evenly and efficiently sterilized.

In the configuration described above, the plurality of spaces to be sterilized may have different volumes, and the first predetermined length of time should preferably be set for each of the spaces to be sterilized in accordance with their volumes. With this configuration, even though there is a difference in volume, the gas concentration can be increased in the plurality of spaces to be sterilized uniformly through the repeated cycles of the filling process.

The plurality of spaces to be sterilized are connected to the gas supply source through a common piping system, and the sensor should preferably be provided in this common piping system. With this configuration, the concentration of nitrogen dioxide gas in the spaces to be sterilized is measured by the same sensor. Therefore, the spaces to be sterilized can be filled with the nitrogen dioxide gas evenly with high precision.

The control device should preferably cause the sensor to detect the concentration of nitrogen dioxide gas in the space to be sterilized that has been excluded from the gas filling process as the concentration therein has reached the predetermined level, every time a second predetermined length of time passes.

Once the concentration of nitrogen dioxide gas in a space to be sterilized that is being filled with gas reaches a predetermined level, this space is excluded from the object to be filled with gas from the next time around. Therefore, if the sensor is provided in the common piping system, the concentration will not be detected during the time when this space is excluded form the object to be filled with gas. A possible drop in the concentration of nitrogen dioxide gas from the prescribed level that may occur as the gas is absorbed by the walls or contents of the space to be sterilized cannot be detected. Therefore, every time the second predetermined length of time passes, the control device causes the sensor to detect the concentration of nitrogen dioxide gas, so that the concentration of nitrogen dioxide gas is kept even in each space to be sterilized, and the sterilization process is thus carried out reliably.

In the configuration described above, the gas supply source, the piping system and the valve device, and the spaces to be sterilized form a closed space. The gas supply source should preferably produce nitrogen dioxide gas from a gas inside this closed space as a material gas by generating plasma.

With the configuration described above, the gas supply source produces nitrogen dioxide gas to be used for sterilization from a gas inside the closed space, which is mainly air, as a material gas by generating plasma. Therefore, the nitrogen dioxide gas concentration can be increased without requiring complex structures such as systems for adjustment of pressure or introduction of outside air.

A gas filling method in a sterilization system according to another aspect of the present invention is a method of filling a plurality of spaces to be sterilized by a sterilization process with nitrogen dioxide gas to be used for the sterilization process, including:

performing a cycle of gas filling process of successively filling each of the plurality of spaces to be sterilized with the nitrogen dioxide gas one by one for a first predetermined length of time;

detecting a concentration of the nitrogen dioxide gas in the plurality of spaces to be sterilized and specifying a gas-filled space to be sterilized in which the nitrogen dioxide gas concentration has reached a predetermined level; and performing further a cycle of gas filling process of successively filling each of the plurality of spaces to be sterilized except for the specified gas-filled space to be sterilized, with the nitrogen dioxide gas one by one for the first predetermined length of time.

With this method, a plurality of relatively wide spaces to be sterilized can be filled with nitrogen dioxide gas evenly and efficiently.

In this case, the method should preferably include a step of detecting the nitrogen dioxide gas concentration in the gas-filled space to be sterilized every time a second predetermined length of time passes.

The invention claimed is:

1. A sterilization system, comprising:
a plurality of spaces to be sterilized by a sterilization process;
a gas supply source generating nitrogen dioxide gas to be used for the sterilization process;
a piping system interposed between the gas supply source and the plurality of spaces to be sterilized;
a plurality of valve devices disposed between the piping system and the plurality of spaces to be sterilized:
a sensor detecting a concentration of the nitrogen dioxide gas in the plurality of spaces to be sterilized; and
a control device configured to control the plurality of valve devices to successively perform a gas filling process to fill each of the plurality of spaces to be sterilized with the nitrogen dioxide gas,
wherein the control device performs the gas filling process including:
a valve control in which while one valve device for one space to be sterilized is opened, the other valve devices for the other spaces to be sterilized are closed, and
the valve control is performed for a predetermined length of time to exclusively connect the one space to be sterilized to the gas supply source and to close off the other valve devices to be sterilized from the one space to be sterilized, the predetermined length of time not being a period of time in which each space to be sterilized is filled with a sufficient concentration of gas in one filling operation, and
the control device repeats the same valve control to a next space to be sterilized as the valve control to the one space to be sterilized so as to perform a cycle of the gas filling process for filling each of the plurality of spaces to be sterilized with the nitrogen dioxide gas one by one, and
when the concentration of the nitrogen dioxide gas in a space to be sterilized is detected by the sensor as being filled with nitrogen dioxide gas by reaching a predetermined level, the control device performs control such that in a next cycle of a gas filling process the space filled with nitrogen dioxide gas is excluded from the gas filling process.

2. The sterilization system according to claim 1, wherein the plurality of spaces to be sterilized have different volumes, and
the predetermined length of time is also set for each of the spaces to be sterilized in accordance with their volumes.

3. The sterilization system according to claim 1, wherein the plurality of spaces to be sterilized are connected to the gas supply source through the piping system, and the sensor is provided in the piping system.

4. The sterilization system according to claim 3, wherein every time a predetermined monitoring interval passes, the control device causes the sensor to detect the concentration of nitrogen dioxide gas in the space to be sterilized that has been excluded from the gas filling process.

5. The sterilization system according to claim 1, wherein the gas supply source, the piping system and the plurality of valve devices, and the plurality of spaces to be sterilized form a closed space, and the gas supply source produces the nitrogen dioxide gas from a gas inside this closed space by generating plasma.

* * * * *